United States Patent [19]

Cohn

[11] Patent Number: 4,797,097
[45] Date of Patent: Jan. 10, 1989

[54] ARTICULATOR FOR DENTAL MODEL

[76] Inventor: Moritz Cohn, 26100 Orchard Lake Rd., Farmington Hills, Mich. 48018

[21] Appl. No.: 38,821

[22] Filed: Apr. 15, 1987

[51] Int. Cl.⁴ .............................................. A61C 11/00
[52] U.S. Cl. ........................................ 433/64; 433/54; 433/60; 433/61
[58] Field of Search .............................. 433/60, 61, 64

[56] References Cited
U.S. PATENT DOCUMENTS 4,299,570 11/1981 Yogosawa .............................. 433/62
4,382,787 5/1983 Huffman ................................ 433/64

*Primary Examiner*—Larry Jones
*Attorney, Agent, or Firm*—Krass & Young

[57] ABSTRACT

A dental articulator includes a pair of attachment members, each adapted to engage a dental casting and a hinge unit including two pivotably interconnected retaining members, each adapted to engage one of the attachment members by means of a joint which may be selectively and reversibly immobilized. The two retaining members are interconnected by a hinge which provides a pair of spaced apart pivot axes for pivoting each of said members and which further provides for the ready and reversible separation thereof.

11 Claims, 3 Drawing Sheets

ARTICULATOR FOR DENTAL MODEL

FIELD OF THE INVENTION

This invention relates to dental technology in general and specifically to an articulator for use with dental cases.

BACKGROUND OF THE INVENTION

Dental articulators are utilized in conjunction with models or castings, the terms being utilized interchangeably herein, in developing prosthodontic dental appliances. In a typical application, a dentist will take an impression of a patient's mouth and utilize this impression to cast a model, which model will be mounted on an articulator to ensure that caps, crowns, bridges or dentures are sized and shaped to coorectly fit in alignment with the remaining piece in the patient's mouth. Dental technicians first fabricate the model and then mount that model on a dental articulator for final finishing and fitting steps.

It is necessary to support such dental models in a relatively natural hinged relationship so as to mimic as closely as possible natural biting movements. If a prosthodontic appliance is not properly shaped, the patient will be forced to undergo multiple adjustments and may possibly damage his or her remaining teeth. A natural bite involves many motions. In addition to normal up and down motions, the human jaw is capable of side to side and back and forth motions, all of which are utilized in eating, drinking and speaking. If a dental articulator cannot simulate all of such motions, the likelihood of fabricating a prosthodontic appliance which will fit comfortably is lessened. Therefore, it is desirable that dental articulators be capable of providing for natural-like jaw movements.

It is also desirable that a dental articulator permit the ready separation of the components of dental models while allowing for their realignment in proper registration. Frequently, it is necessary for dental technicians to perform precise and detailed work on prosthodontic appliances mounted onto dental articulators. If these models are affixed to an articulator which does not permit their separation, such adjustments become very difficult. Accordingly, it will be appreciated that the quality of a prosthodontic appliance will be improved and the quantity of time taken for its production will be decreased if an articulator which allows for separation of the models is employed.

There are a wide variety of dental articulators of varying degrees of sophistication presently available. The most simple of such articulators allow for mere pivotal motion of models relative to one another whereas more sophisticated models provide for a full range of occlusal movement. The simple models of articulators are relatively easy to use, small, lightweight and cheap and frequently are fabricated as disposal items. However, such articulators do not allow for a full range of occlusal motion; furthermore these are permanently attached to the models using plaster or glue, such as cyanoacrylate. In contrast, the more sophisticated articulators are large, complicated and expensive to assemble devices which frequently necessitate precise mounting hardware be affixed to dental models used therewith. Expense is a limiting factor in the use of such articulators insofar as it will be appreciated that a single articulator will be effectively tied up for the entire period of time in which an appliance is being manufactured. To equip a dental laboratory with a sufficient number of such aritculators to enable the output of a high volume of work involves a very considerable expense.

U.S. Pat. No. 4,382,787 discloses a simple, disposable dental articulator. The articulator of the U.S. Pat. No. 4,382,787 is fabricated from a flexible polymeric material and, while the mechanical arrangement of parts of that articulator only allows for simple pivotal motion of dental models, the flexibility of the polymeric material allows for some degree of additional occlusal motion. The articulator disclosed therein is affixed to a pair of dental models by means of ball joints and when proper registration of the models is obtained, the joints are rendered permanently immobile by the injection of an adhesive thereinto. Because of this immobilization, any further adjustment necessitates complete replacement of the articulator. It will additionally be noted that the articulator is essentially destroyed in the process of use and may not be reused.

It will thus be appreciated that there is still a need for a simple, low-cost, reusable dental articulator which readily simulates a full range of occlusal motion and which may be readjusted once affixed to a dental model. It is further desired that such an articulator allow for complete separation of one or both halves of the dental model, and be capable of resisting the stresses imposed by occlusal movements during the fabrication of dental appliances. It is further desired that such an articulator not rely upon the use of plaster or adhesives for affixing the positional relationship of the models attached thereto.

The present invention provides a dental model articulator securing these advantages. The articulator disclosed herein is simple, low in cost, and adjustable over a full range of motion. The articulator includes a pair of joints affixable to the dental models, which joints may be selectively and reversably immobilized so as to allow for adjustment of the articulator during use as well as allowing for removal of the articulator from the model for reuse. Additionally, the articulator of the present invention allows for the ready and reversible separation of the dental castings as well as the replacement of said castings in their previous registration. These and other advantages of the present invention will be readily apparent from the drawings, description, and claims which follow.

SUMMARY OF THE INVENTION

There is disclosed herein a dental articulator for hingably retaining a pair of dental castings. The articulator comprises a pair of attachment members, each member adapted to engage one of the castings as well as a hinge unit including two pivotally interconnected retaining members, each adapted to engage one of the attachment members by means of a joint which may be selectively and reversably immobilized. The hinge unit further includes a hinge connection which provides a pair of pivot axes disposed in spaced apart parallel relationship, so that each retaining member is oriented to pivot about one of the axes; the hinge unit further provides for the ready and reversible separation of the retaining members. In one particular embodiment, the retaining members pivotally engage the attachment members by means of at least one ball and socket joint. In some embodiments, the ball portion of the joint is located on the retaining member and the socket on the attachment member whereas in other instances, the ball is on the attachment member and the socket on the retaining member. The joint may be selectively or reversably immobilized by means of a locking screw associated therewith and the attachment member may in some instances include a pin adapted to be implanted in the dental casting.

In other particular embodiments, the retaining members are generally T-shaped members, each of which includes a pair of journal bearings disposed on opposite ends of the crossbar of the T, each pair of bearings defining one of the pivot axes. In this embodiment, the journal bearings associated with a first T-shaped member are maintained in spaced apart relationship from corresponding journal bearings associated with a second T-shaped member by means of a pair of spacer bars. In yet other embodiments, the spacer bars are fixedly attached to the first pair of journal bearings associated with a first T-shaped member and removably attached to the second pair of journal bearings associated with a second member so as to allow for ready separation thereof. Such removable mounting may be accomplished by providing one end of the spacer bars with a ball-shaped tip and providing one of the journal bearings with a socket adapted to receive the ball tip. The socket in the journal bearing may be formed as an elongated socket so as to allow for lateral displacement of the journal bearing and the T-shaped member associated therewith. In other instances, the journal bearing may be provided with a channel adapted to engage the shaft bearing the ball-shaped tip so as to immobilize that joint.

DETAILED DESCRIPTION OF THE PREFERRED EMBODIMENT

Figure 1:
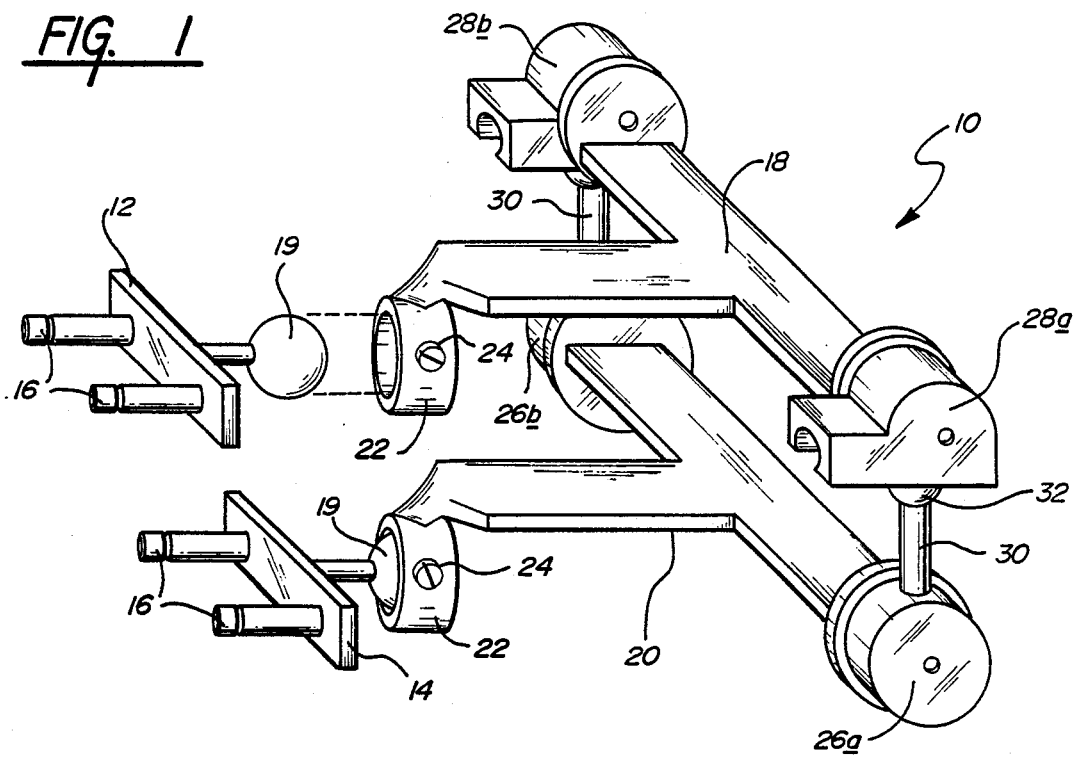
FIG. 1 is a perspective view of one embodiment of the articulator structured in accord with the principles of the instant invention showing one of the pair of attachment members as detached from its corresponding retaining member.

Referring now to FIG. 1, there is shown in perspective view one particular embodiment of articulator 10 structured in accord with the principles of the instant invention. The articulator 10 is adapted to retain a pair of dental castings, (not shown in this Figure) in a predetermined hinged relationship. Furthermore, the articulator 10 is adapted to allow for the dental castings to be separated, so as to allow for various operations to be carried out thereupon and to allow the castings to be returned to their previously aligned postions after said operations are complete.

The articulator 10 includes a pair of attachment members 12,14 each adapted for connection to one of a pair of dental castings, and further adapted for pivotal interconnection to the remainder of the articulator. As illustrated, a first one of the attachment members 12 is shown separated from the remainder of the articulator. It will be noted that, in this embodiment, the attachment member 12 includes a pair of mounting pins 16 adapted to be implanted into the dental casting as, for example, during fabrication of the casting. The attachment members further include a projecting ball 19, which mounts into a corresponding socket as will be discussed in greater detail below.

The main body of the articulator is comprised of a hinge unit which includes two pivotally interconnected retaining members 18,20. As illustrated, the retaining members 18,20 are generally T-shaped members, each provided with a socket joint 22 at the base of the T. The socket joint 22 is adapted to receive and retain the ball 19 of the attachment member 12,14. The socket 22 is further provided with a locking screw 24 disposed so as to immobilize the ball 19 within the socket 22.

As illustrated, the locking screw 24 is a set screw although obviously other such locking devices may be employed as will be apparent to one of skill in the art. For example, the socket 22 may be in the form of a collar encircling the ball 19 and the locking screw 24 may function to decrease the diameter of the collar so as to rigidify the joint. In yet other embodiments, the retaining members 18,20 may be affixed so the attachment members 12,14 by other joints provided that such joints allow for pivotable attachment as well as being capable of being selectively and reversibly immobilized. For example, in keeping with the principles of the present invention, attachment may be by means of two or more ball joints so as to allow for a higher degree of flexibility. Similarly, a universal joint provided with a set screw or other such means for immobilization or a pair of conventional hinge members disposed at angles to one another and provided With a means for immobilization may also be employed. All of such variations will be readily apparent to one of skill in the art.

In addition to being pivotably interconnected to the attachment members 12,14, the retaining members 18,20 are hingedly interconnected in a manner which allows for the ready and reversible separation thereof. Toward the end, each of the attachment members 18,20 is provided with a pair of journal bearings disposed on distal ends of the crossbar of the T. The first retaining members 20 has a first pair of journal bearings 26a,26b disposed on distal ends of the crossbar of the T. A second retaining member 18 has a second pair of journal bearings 28a, 28b similarly disposed on distal ends of the T. It should be noted at this point that the termjournal bearing as used herein is meant to include any bearing unit adapted to receive a shaft-like member for rotation therein and includes bearing members such as sleeve bearings, ball bearings, roller bearings and the like as well as the housing for such bearings. Each pair of journal bearings 26a,26b and 28a, 28b provide a pivot axis therebetween, in which axis the attachment member 18,20 is free to rotate. For example, the first retaining member 20 pivotally rotates along an axis established between journal bearing 26a and journal bearing 26b. The two pairs of bearings thus provide a pair of pivot axes disposed in spaced apart relationship, each axis associated with a given retaining member. In keeping with the spirit of the present invention, only one of the attachment members 18,20 may have a set of bearings associated therewith, the other being fixed; such an arrangement will still allow for sufficient relative motion between the members.

The two pairs of journal bearings are interconnected by spacer bars such as the illustrated connecting rods 30 extending therebetween. As depicted, journal bearing 26a is connected to journal bearing 28a by a first connector rod 30, and journal bearing 26b is interconnected to journal bearing 28b by a second connector rod 30. It will be noted that the second pair of journal bearings 28a,28b are of different shape than the first set of journal bearings 26a,26b. The second set of journal bearings 28a,28b include therein a socket adapted to receive a ball-shaped protrusion 32 on the terminal end of the connecting rod 30. It is generally preferred that the socket associated with the journal bearing be formed in a generally elongated configuration so as to allow the ball 32 to slide therewithin.

Use of such an elongated socket permits the first and second retaining members 18,20 to be translationally displaced in parallel planes so as to permit adjustment of dental models attached thereto, and further allows for saggital movement of the articulator so as to simulate natural dentition. Additionally, the elongated socket facilitates separation and reattachment of the two retaining members 18,20. Particular details of the journal bearings 28a, 28b will be elaborated on in further detail hereinbelow.

Figure 2:
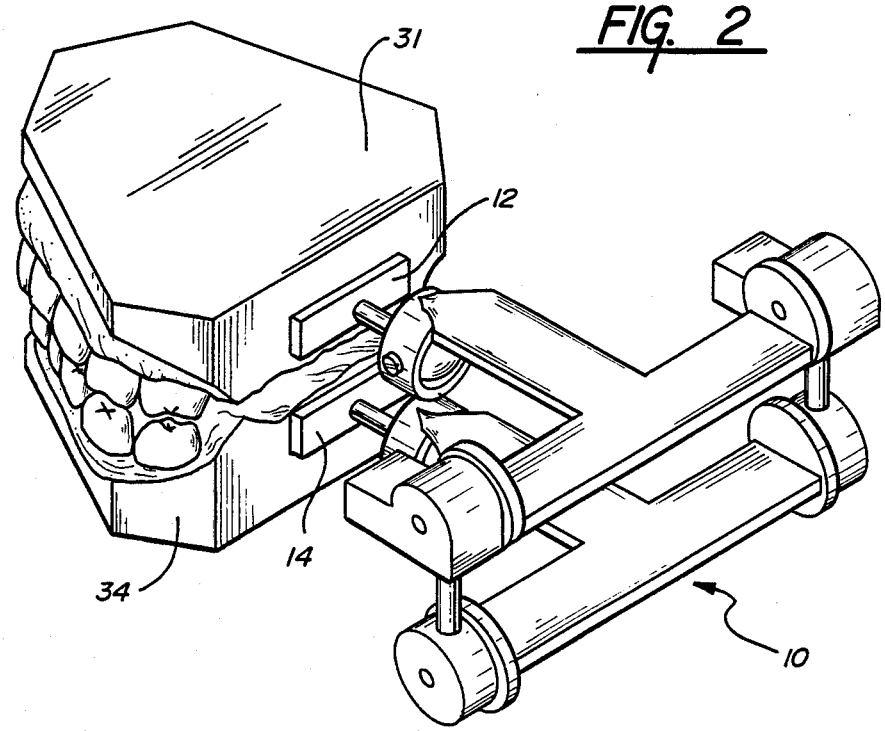
FIG. 2 is a perspective view of the articulator of FIG. 1 as attached to a pair of dental castings.

Referring now to FIG. 2, there is shown a perspective view of a dental articulator 10, generally similar to that discussed with reference to FIG. 1 showing its attachment to a pair of dental models 31,34. As depicted, a first attachemnt member 12 is attached to the first casting 31, and a second attachment member 14 is attached to a second casting 34. As discussed previously, such attachment may be effected by directly casting the attachment members 12,14 into the model as it is being made, relying upon retaining pins to maintain the attachment. Alternatively, the attachment members 12,14 may be cemented to the dental castings 31,34 by means of plaster, epoxy or other such adhesive material. Obviously, other modes of attachment may be employed as, for example, screws or pins may be utilized.

In the use of the articulator 10, the attachment members 12,14 are first affixed to the castings 31,34 and then the retaining units are affixed to the attachment members. The two castings 31,34 comprising the dental model are then adjusted so as to achieve a proper "bite" relationship. That is to say the teeth of the model are placed in proper alignment. Once such alignment is achieved, the joints interconnecting the retaining members to the attachment members are immobilized as, for example, by turning the locking screws associated therewith. Such immobilization affixes the castings 31,34 in the desired relationship. It will be appreciated that the journal bearings, the slots therein, and ball tipped shaft all cooperate to allow for a full range of occlusal action.

As the dental technician carries out operations on the articulated castings, it may become necessary to separate those castings. The articulator of the present invention allows for the ready separation of the two retaining members at the point where the journal bearings are attached. Separation may be accomplished by popping the attachment ball 32 out of the socket in its corresponding journal bearing 28a,28b or by simply sliding the attachment ball 32 out of the elongated socket. Additionally, separation can be accomplished by releasing the ball 19 from the socket 22. After operations are complete, the castings 32,34 may be rejoined in their previous relationship by reinserting the attachment ball 32 into the socket of the journal bearings. In many instances, the bit relationship will have to be adjusted as the fabrication of the appliance proceeds. Such adjustment may be readily accomplished by adjusting the screw 24 holding the ball 19 in the socket 22. This is in contrast to previously employed articulators wherein the attachment is rigidly established by adhesive, plaster or the like.

Figure 3:
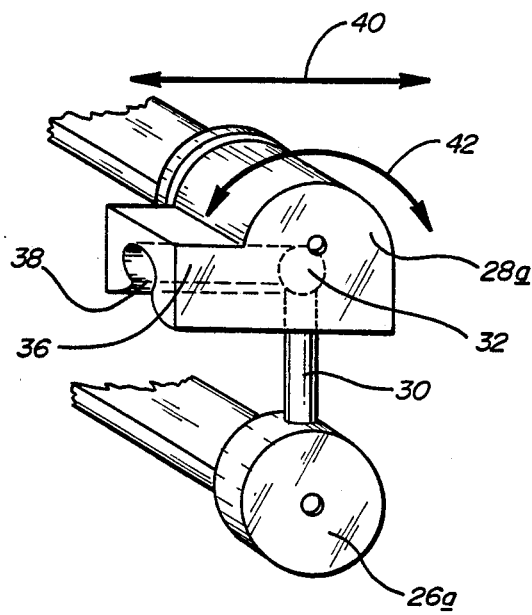
FIG. 3 is a perspective view of a portion of the articulator of the present invention depicting in greater detail the manner in which the journal bearings of the two retaining members are interconnected so as to allow for ready separation thereof.

Referring now to FIG. 3, there is shown a more detailed view of one member of each pair of journal bearings illustrating the manner in which they are removably attached. Illustrated is a first journal bearing 26a having affixed thereto a shaft 30 which terminates in a ball-shaped portion 32 illustrated in phantom outline. The shaft 30 is rigidly affixed to the journal bearing 26a and may be formed by drilling into the housing of the journal bearing 26a and inserting the rigid rod thereinto or it may be formed as an integral part of the housing, as for example, during the casting thereof. The housing of the second journal bearing 28a is shaped so as to include an elongated socket 36 therein, as indicated by the phantom outline. As shown, the elongated socket 36 is configured so as to retainably receive the ball 32 of the shaft 30. The elongated socket 36 extends to and through the outermost edge of the housing of the journal bearing 28 so as to form an opening 38 therein.

The elongated channel 36 allows for forward and backward translational movement of the journal bearing 28 as indicated by the arrow 40. Such back and forth movement is necessary to permit proper alignment of the dental casting as well as to simulate occlusal action. The ball 32 and the elongated socket 36 also permit rotational movement of the entire journal bearing 28a relative to the other journal bearing 26a in a direction indicated by the curved arrow 42. Such a range of motion further allows for positioning and occlusal simulation.

In order to disassemble the journal bearings, the ball 32 may be slid along the elongated socket 36 and out the opening 38 at the terminus thereof. Alternatively, the socket 36 may be fabricated so as to allow the ball 32 to be popped therefrom. Reassembly of the journal bearing will obviously occur by a reverse process.

The elongated socket 36 may in some embodiments, be configured so as to be capable of receiving and retaining the shaft 30 attached to the lower journal bearing 36a. Such attachment could readily be accomplished by rotating the upper journal bearing 28a in a counter-clockwise direction corresponding to the arc of arrow 42. When so disposed, the shaft 30 will snap into the elongated socket 36. In this embodiment, the dental castings may be positioned in proper registration with the upper journal bearing 28 in its free position as illustrated and once such registration is achieved, the upper journal bearing 28 may be rotated to snap the shaft 30 into the socket 36 so as to fix the position. The retaining members will still be capable of pivoting along axes defined by the journal bearing therefrom permitting relative motion of the dental castings.

Figure 4:
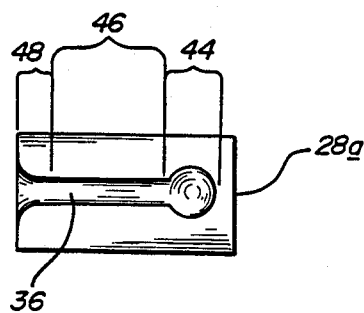
FIG. 4 is a bottom plan view of one of the journal bearings as adapted to removably engage a ball-like member affixed to a corresponding journal bearing.

Referring now to FIG. 4, there is shown a bottom plan view of one of the upper journal bearings 28a illustrating more clearly the configuration of one elongated socket formed therein. The socket 36 includes a generally hemispherical depression 44 therein adapted to allow for the ball portion 32 of the rod 30 to be popped thereinto. The socket 36 further includes a generally linear central portion 46 adapted to allow for sliding of the ball 32 therealong and/or configured so as to receive and retain the shaft of the rod 30 therein. In the illustrated embodiment, the terminal portion of the elongated socket 48 is formed as an outwardly flaring member so as to allow for the ball 32 of the shaft 30 to be readily slid thereinto. Obviously, other configuraitons of elongated sockets may be employed in the practice of the instant invention; for example, the socket may be of uniform elongated shape or of a tapering elongated shape. In yet other embodiments, the socket may not be elongated, or in yet other embodiments may include a set screw or similar means for rigidly fixing the position of the ball 32 therein. All of such variations are within the knowledge and capability of one of skill in the art.

Figure 6:
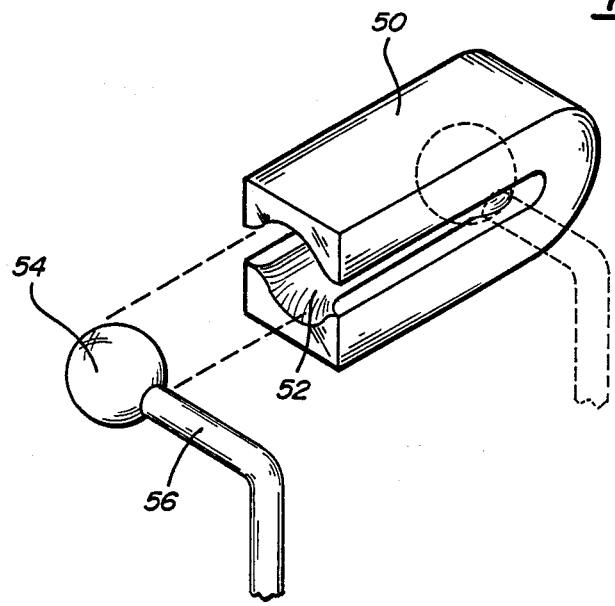
FIG. 6 is a perspective view of another attachment for removably affixing the two attachment members of the articulator.

Referring now to FIG. 6, there is shown yet another ball and socket joint which may be advantageously employed in conjunction with the present invention. The joint includes an elongated socket 50, having a channel 52, therein configured to receive a ball 54. The socket 50 is a clip-like member having an open channel passing therethrough. Presence of such an opening allows the socket 50 to retain the ball 54 tightly, while still permitting sliding and rotating motion thereof. As will be noted, the ball 54 is mounted on a shaft 56 having a right angle bend therein. Such an arrangement allows the shaft 56 to pass through the opening in the socket 50 so as to allow attachment to the remainder of the articulator as described hereinabove. The socket 50, of FIG. 6 may be mounted on either of the journal bearings, as previously described. In one embodiment, the socket 50 can be affixed by the upper (non-slit) side thereof, and in that instance the right angled shaft 56 will be employed. In other embodiments, mounting will be along the slit bearing side and a straight ball shaft can be utilized. Obviously, other means may be employed to affix the two sets of journal bearings, in keeping with the principles disclosed herein. For example a non-sliding simple press-fit socket joint wherein a ball or pin is retained in a socket can be similarly utilized. It will also be readily appreciated that the ball and socket joint of FIGS. 4 and 6 can permit sufficient pivoting of the attachment members so as to obviate need for journal bearings.

Figure 5:
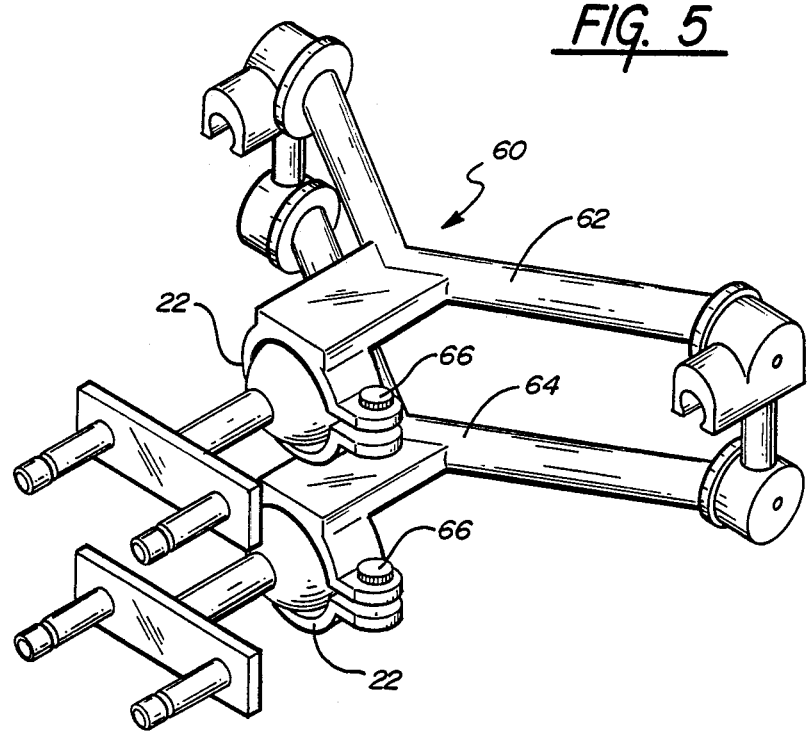
FIG. 5 is a perspective view of another embodiment of an articulator structured in accord with the principles of the instant invention.

Referring now to FIG. 5, there is shown another configuration of articulator 60, structured in accord with the principles disclosed herein, and illustrating the fact that various designs of articulators are possible within the scope of the present invention. The articulator 60 of FIG. 5 is generally similar to that of FIGS. 1 and 2 and accordingly, similar structures will be referred to by similar numbers. Where the articulator 60 differs from that previously described is that the attachment members 62,64 are generally Y-shaped members, having a relatively short tongue or base portion. Such an arrangement places the models closer to the pivot axes of the Y-shaped members 62,64. Furthermore the arms of the Y allow for a high degree of flexibility and hence better occlusal simulation.

The articulator 60 also includes sockets 22 having an immobilizing thumb screw 66 accessible from the top thereof, so as to faciliate adjustment. Obviously, other socket designs could be similarly employed. Other arrangements could be similarly employed, for example, the socket 22 could include a split, threaded shaft adapted to engage a threaded collar so as to permit manual adjustment thereof. For example, the ball 19 could be surrounded by two or three encircling bands. Additionally, the ball 19, could be split partially therethrough so as to confer a degree of compressability or flex thereto.

The articulator of the present invention may be fabricated from a wide variety of materials. There are presently available a wide variety of low cost synthetic polymeric materials having a high degree of strength, and durability which are capable of being molded into precise configurations. It is anticipated that such materials may be advantageously employed in fabricating the articulator of the present invention. Included among such materials are nylon-based polymers, acrylic polymers, styrene polymers, polyvinylchloride and the like. It is further anticipated that in some instances it may be advantageous to fabricate all or part of the articulator from metallic materials. Obviously, many variations are possible within the scope of the present invention. For example, the journal bearings may be replaced with hinges, ball joints or similar members. The retaining members may be fabricated in a wide variety of configurations other than the T-shaped configuraiton shown herein, and the articulator may have further attachment means adapted to secure it to support bases, motor drives and other such ancillary equipment. All of such modifications and variations are anticipated in light of the disclosure herein. It will therefore be understood that the foregoing drawings, description and discussion are merely meant to be illustrative of the principles of the present invention and not limitations on the practice thereof. It is the following claims, including all equivalents, which define the scope of the invention.

I claim:

1. A dental articulator for hingedly retaining a pair of dental castings, said articulator comprising:
    a pair of attachment members, each adapted to engage one of said castings, and,
    a hinge unit including two pivotally interconnected retaining members, each adapted to pivotally engage one of said attachment members by means of at least one ball and socket joint, the socket of which includes a locking screw for selectively and reversibly immobilizing said joint;
    said hinge unit further including a hinge connection which (a) provides a pair of pivot axes disposed in spaced-apart parallel relationship, each retaining member adapted to pivot about one of said axes, and which (b) provides for the ready and reversible separation of said retaining members.

2. A dental articulator as in claim 1, wherein a ball is provided on each of said retaining members and a socket is provided on each of said attachment members.

3. A dental articulator as in claim 1, wherein a ball is provided on each of said attachment members and a socket is provided on each of said retaining members.

4. A dental articulator as in claim 1, wherein each of said attachment members includes at least one pin adapted to be implanted in said casting.

5. A dental articulator as in claim 1, wherein said retaining members are generally T-shaped.

6. A dental articulator as in claim 1, wherein said hinge unit includes two pairs of journal bearings, each defining one of said pivot axes, the first pair adapted to pivotally support the first retaining member and the second adapted to pivotally support the second retaining member, said first and second pairs of journal bearings maintained in spaced apart relationship by a pair of spacer bars.

7. A dental articulator as in claim 6, wherein said spacer bars are fixedly attached to the first pair of journal bearings and removably attached to the second pair of journal bearings.

8. A dental articulator as in claim 7, wherein each of said spacer bars includes a generally elongated shaft having a ball tip thereupon and wherein each of said second journal bearings includes a socket adapted to retainably receive the ball tip.

9. A dental articulator as in claim 8, wherein the socket in said second journal bearing is a generally elongated socket and wherein said ball is adapted to slide in said socket.

10. A dental articulator as in claim 8, wherein said socket includes a channel communicating therewith, said channel adapted to retainably receive the elongated shaft.

11. A dental articulator for hingedly retaining a pair of dental castings, said articulator comprising:

a pair of attachment members, each adapted to engage one of said castings and each further including a projecting ball adapted to engage a socket;

a hinge unit comprised of two T-shaped members, each including (a) a socket located at the base of the T and adapted to receive and retain the projecting ball of one of said attachment members, each socket including a locking screw to selectively and reversibly immobilize the ball in said socket, and (b) a pair of journal bearings located at opposite ends of the crossbar of the T and adapted to pivotably retain the crossbar therein;

said hinge unit further including a pair of generally elongated rod-like members fixedly attached to each of the pair of journal bearings associated with a first T-shaped member, the unattached end of said rod-like members terminating in a ball, and wherein the pair of journal bearings of a second T-shaped member each have an elongated socket adapted to receive and retain the ball therein, whereby said rod-like member, channel and socket cooperate to removably retain said T-shaped members in a pivotable relationship.

* * * * *